(12) United States Patent
Tsukada et al.

(10) Patent No.: US 11,678,827 B2
(45) Date of Patent: Jun. 20, 2023

(54) COMPOSITE WIRING, CAPACITANCE SENSOR, MULTIPLEXING CABLE, AND WIRING FOR INCORPORATION INTO ELEMENT

(71) Applicant: NIPPON TELEGRAPH AND TELEPHONE CORPORATION, Tokyo (JP)

(72) Inventors: Shingo Tsukada, Atsugi (JP); Hiroshi Nakashima, Atsugi (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 209 days.

(21) Appl. No.: 16/761,772

(22) PCT Filed: Nov. 13, 2018

(86) PCT No.: PCT/JP2018/041951
§ 371 (c)(1),
(2) Date: May 5, 2020

(87) PCT Pub. No.: WO2019/098182
PCT Pub. Date: May 23, 2019

(65) Prior Publication Data
US 2021/0177332 A1    Jun. 17, 2021

(30) Foreign Application Priority Data

Nov. 15, 2017   (JP) ............................. JP2017-220479

(51) Int. Cl.
*H01B 7/06* (2006.01)
*A61B 5/256* (2021.01)
(Continued)

(52) U.S. Cl.
CPC .............. *A61B 5/256* (2021.01); *A61B 5/282* (2021.01); *A61B 5/6802* (2013.01); *H01B 7/06* (2013.01)

(58) Field of Classification Search
CPC ....... A61B 5/256; A61B 5/282; A61B 5/6801; A61B 5/6802; A61B 5/6804; A41D 1/005; H01B 7/06
See application file for complete search history.

(56) References Cited

U.S. PATENT DOCUMENTS

| | | | |
|---|---|---|---|
| 2008/0038512 A1* | 2/2008 | Burr | B32B 3/04 428/137 |
| 2014/0100469 A1* | 4/2014 | Sagalovich | A61B 5/6805 600/300 |

FOREIGN PATENT DOCUMENTS

| | | |
|---|---|---|
| JP | S57-017007 U | 1/1982 |
| JP | S59-118228 U | 8/1984 |

(Continued)

OTHER PUBLICATIONS

Ono et al., Highly conductive membrane wiring board—Fujikura Co., Ltd., Fujikura Technical Review, No. 107, pp. 79-83, 2004.
(Continued)

*Primary Examiner* — Benyam Haile
(74) *Attorney, Agent, or Firm* — Harness, Dickey & Pierce, P.L.C.

(57) ABSTRACT

A composite wiring includes a plurality of pieces of wiring accommodated and gathered together within an elastic sheath, wherein at least one of the pieces of wiring is elastic wiring including an elastic tube, a conductor wire arranged within the tube, and fixing portions for fixing the conductor wire and the tube at both ends of the tube in the lengthwise direction thereof, the length of the conductor wire between the fixing portions when the tube is in an unextended state
(Continued)

being longer than the length of the tube between the fixing portions.

6 Claims, 6 Drawing Sheets

(51) Int. Cl.
*A61B 5/282* (2021.01)
*A61B 5/00* (2006.01)

(56) References Cited

FOREIGN PATENT DOCUMENTS

| JP | H05-043420 U |   | 6/1993  |         |
|----|--------------|---|---------|---------|
| JP | H05-043420 U | * | 11/1993 | ............... H01B 7/06 |
| JP | 2007026714 A |   | 2/2007  |         |
| JP | 2012227061 A |   | 11/2012 |         |
| JP | 201750155 A  |   | 3/2017  |         |
| JP | 2017121442 A |   | 7/2017  |         |

OTHER PUBLICATIONS

Kanehiro et al., Development of our flexible printed circuit business, SEI Technical Review, No. 172, pp. 1-9, Jan. 2008.
International Search Report (in English and Japanese) issued in International Application PCT/JP2018/041951, dated Dec. 11, 2018; ISA/JP.
Japanese Notice of Allowance from counterpart JP2019554221, dated Jun. 30, 2020.

* cited by examiner

COMPOSITE WIRING, CAPACITANCE SENSOR, MULTIPLEXING CABLE, AND WIRING FOR INCORPORATION INTO ELEMENT

CROSS-REFERENCE TO RELATED APPLICATIONS

This application is a 371 National Phase of International Application No. PCT/JP2018/041951, filed on Nov. 13, 2018, which claims priority to Japanese Application No. 2017-220479, filed on Nov. 15, 2017. The entire disclosures of the above applications are incorporated herein by reference.

TECHNICAL FIELD

The present invention relates to a composite wiring, a capacitance sensor, a multiplexing cable, and wiring for incorporation into an element.

BACKGROUND ART

In for example a medical device, a health device, a physiological function testing device, or a research device that acquires an electrical biological signal such as an electrocardiograph or an electroencephalograph, the electrical signal is transmitted and received between a bioelectrode in contact with the body and the device. Therefore, the bioelectrode and the device are connected by wiring (for example, Non-Patent Documents 1 and 2). When the wiring is placed in an unstable state at a position away from the body, noise due to body movement or wiring vibration is picked up and the signal-to-noise ratio (S/N ratio) tends to deteriorate. On the other hand, a living body has a large capacitance, and so a shielding effect can be obtained in the vicinity of the body. Therefore, the portion of the wiring on the bioelectrode side is usually fixed along the surface of the body.

The wiring, due to generally being non-elastic and relatively rigid, is manufactured with a long length having slack, with the remainder of the wiring often being bundled and fixed to the body at multiple locations using adhesive tape or the like. However, since the wiring is rigid, a sense of discomfort is likely to arise at the time of wearing. In particular, wiring of a medical standard is often heavy and hard due to demands such as withstanding voltage, tensile strength, and suppression of impedance fluctuations, and so such wiring is likely to be subject to vibration and impart a great sense of discomfort when touching the skin.

In wearable biosignal acquisition devices such as belt-type and clothing-type wearable bioelectrodes, wiring such as conductive thread or a metal wiring material is directly sewn or pasted on the fabric of the item, or accommodated in a storage space with a tunnel structure or a double structure provided in the item. However, since the wiring has poor elasticity and is rigid, the stretchability of the fabric is impaired at the portion where the wiring is attached, and the comfort becomes worse. In order to impart stretchability to the part where the wiring is attached, measures such as sewing the wiring in a zigzag shape may be taken. However, in addition to a sufficient effect often not being obtained, a decrease in productivity and workability that results from performing such measures poses a problem.

Also, wearable biological signal acquisition equipment has insufficient waterproofness of the wiring, making it difficult to measure biosignals such as electrocardiograms and electromyograms when the wiring gets wet due to swimming, bathing, sweating, rain, or the like. Therefore, the wiring is also required to have excellent waterproofness.

When a heart attack, convulsive cramping of skeletal muscle, and convulsion seizures due to epilepsy and the like occur, prompt action is required. Recent years have seen increasing opportunities for middle-aged and senior citizens to exercise in pools and hot spring facilities for rehabilitation and health promotion, so it is also necessary to respond quickly to accidents during exercise. In addition, in order to prevent heat stroke, it is necessary to manage the perspiration state when going back and forth between an air-conditioned room or vehicle and the outside. Therefore, there is a need for wiring that can handle various functions such as detecting these events simultaneously, giving notice of the detected information, and issuing a warning.

As a wiring having functionality, there is also a method using a resin film such as a polyethylene terephthalate film. However, this method is unsuitable for practical use because the wiring easily curls, leading to substantial discomfort.

PRIOR ART DOCUMENTS

Non-Patent Documents

[Non-Patent Document 1] "Highly conductive membrane wiring board—Fujikura Co., Ltd.", Fujikura Technical Review, no. 107, pp. 79-83, 2004.

[Non-Patent Document 2] "Development of our flexible printed circuit business", SEI Technical Review, no. 172, pp. 1-9, Jan. 2008.

SUMMARY OF THE INVENTION

Problems to be Solved by the Invention

An object of the present invention is to provide a composite wiring that has excellent curl resistance, waterproofness, and elasticity, hardly impairs the elasticity of fabric even when applied to clothing, can reduce discomfort when worn, and is applicable to various functions, and a capacitance sensor, a multiplexing cable, and a wiring for incorporation into an element using the composite wiring.

Means for Solving the Problems

A composite wiring of one embodiment of the present invention is a composite wiring including a plurality of pieces of wiring accommodated and gathered together within an elastic sheath, at least one of the pieces of wiring being elastic wiring provided with an elastic tube, a conductor wire arranged within the tube, and fixing portions for fixing the conductor wire and the tube at both ends of the tube in the lengthwise direction thereof, the length of the conductor wire between the fixing portions when the tube is in an unextended state being longer than the length of the tube between the fixing portions.

A capacitance sensor of one embodiment of the present invention is formed from the composite wiring, in which two pieces of elastic wiring are accommodated in the sheath as the wiring.

A multiplexing cable of one embodiment of the present invention is formed from the composite wiring.

A wiring for incorporation into an element of one embodiment of the present invention is formed from the composite wiring, in which pieces of wiring are connected to each other via a notifying means or a measuring means in the sheath.

A garment of one embodiment of the present invention, to which the composite wiring is fixed.

Advantageous Effects of the Invention

The composite wiring according to the present invention has excellent curl resistance and waterproofness as well as excellent elasticity, does not easily impair the elasticity of fabric even when applied to clothing, and can be suitably used as a capacitance sensor, a multiplexing cable, and wiring for incorporation into an element.

EMBODIMENTS FOR CARRYING OUT THE INVENTION

The dimensions and the like illustrated in the following description are merely examples, and the present invention is not necessarily limited thereto, and can be appropriately modified and implemented within a scope of not changing the gist thereof.

[Composite Wiring]

The composite wiring according to an embodiment of the present invention is a wiring in which a plurality of pieces of wiring are accommodated and gathered together within an elastic sheath. In the composite wiring according to one embodiment of the present invention, at least one of the pieces of wiring accommodated in the sheath is elastic wiring. The elastic wiring is wiring in which, in the state of the conductor wire arranged within the elastic tube, the conductor wire and the tube are fixed at each of both ends in the lengthwise direction of the tube, and the length of the conductor wire between fixing portions when the tube is in an unextended state is longer than the length of the tube between the fixing portions.

Hereinafter, the composite wiring according to the first aspect of the present invention will be described by illustrating an example.

Figure 1:
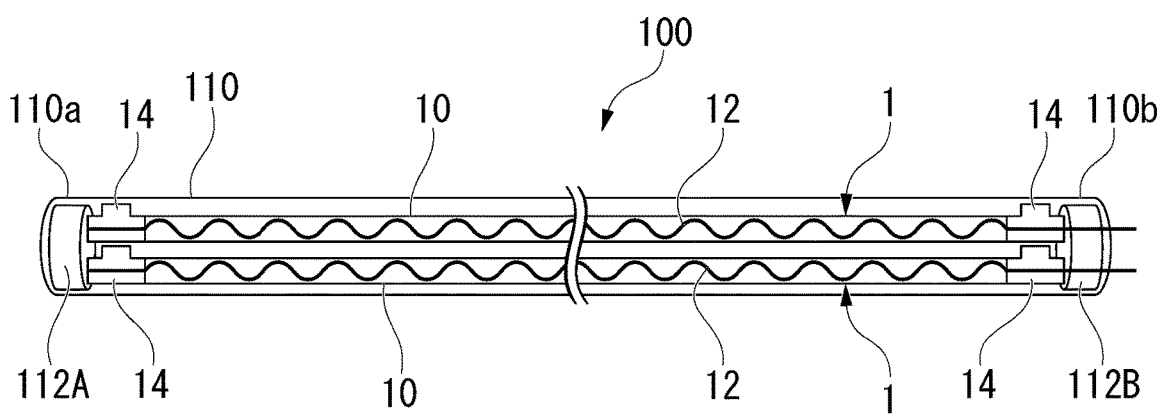
FIG. 1 is a side view showing the composite wiring according to an embodiment of the present invention.

As shown in FIG. 1, a composite wiring 100 according to the present embodiment is provided with a sheath 110, and two pieces of elastic wiring 1 arranged and accommodated within the sheath 110.

Figure 2:
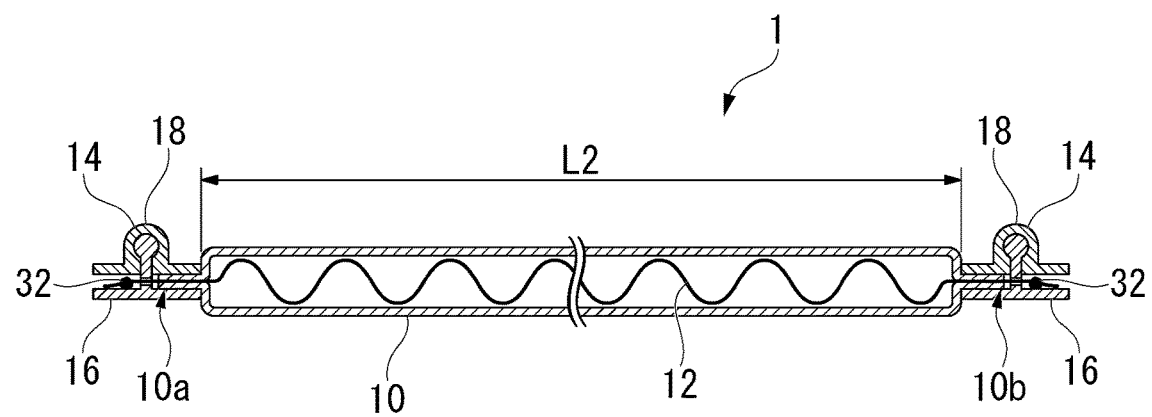
FIG. 2 is a cross-sectional view showing the elastic wiring used for the composite wiring of FIG. 1.

As shown in FIGS. 1 and 2, the elastic wiring 1 is provided with a tube 10, a conductor wire 12, and a caulking member 14.

The conductor wire 12 is arranged within the tube 10 so as to extend from a first end portion 10a to a second end portion 10b of the tube 10 in the lengthwise direction thereof. In the elastic wiring 1, the conductor wire 12 and the tube 10 are fixed by caulking by the caulking member 14 at both ends of the tube 10 in the lengthwise direction, namely, the first end portion 10a side and the second end portion 10b side.

The tube 10 has elasticity. That is, the tube 10 is a tube that hardly breaks when extended by application of a load in the lengthwise direction thereof, and has little residual displacement upon contracting when the load is removed. The elasticity of the tube 10 can be adjusted by the material and thickness of the tube 10.

As a material for forming the tube 10, an insulating material having elasticity can be used. For example, various elastomers such as silicone rubber, urethane rubber, natural rubber, isoprene rubber, butadiene rubber, styrene-butadiene rubber, chloroprene rubber, nitrile rubber, polyisobutylene, ethylene propylene rubber, chlorosulfonated polyethylene, acrylic rubber, fluorine rubber, and epichlorohydrin rubber can be used. As a material for forming the tube 10, silicone rubber is preferable from the viewpoint of heat resistance. As a material for forming the tube 10, one type may be used alone, or two or more types may be used in combination.

The extension at breakage of the tube 10 is preferably 25 to 300%, and more preferably 50 to 150%. If the extension at breakage of the tube 10 is equal to or greater than the lower limit of the above range, the elasticity of the elastic wiring 1 is improved and the sense of discomfort is further reduced. If the extension at breakage of the tube 10 is less than or equal to the upper limit of the above range, it is possible to avoid breakage and short circuiting of the wiring due to stress applied to the wiring as a result of extension of the wiring during mounting of the wiring.

The extension at breakage of the tube is measured according to JIS K-7127 (1999).

The inner diameter and the outer diameter of the tube 10 are not particularly limited, and may be set as appropriate so that the conductor wire 12 can be disposed in the tube 10. For example, the inner diameter of the tube 10 can be 0.1 to 10 mm, and the outer diameter can be 0.2 to 12 mm.

The thickness of the tube 10 is preferably 0.1 to 1 mm, and more preferably 0.2 to 0.6 mm. If the thickness of the tube 10 is equal to or greater than the lower limit of the above range, sufficient strength can be easily obtained.

If the thickness of the tube 10 is less than or equal to the upper limit of the above range, excellent elasticity is easily obtained.

As a material for forming the conductor wire 12, materials generally used for conductor wires can be used, and examples thereof include stainless steel (SUS), enamel, gold, platinum, and iridium. Among these, SUS is preferable as a material for forming the conductor wire 12 because it is not easily rusted, has excellent heat resistance, and can be washed when applied to clothing. The material for forming the conductor wire 12 may be one type or two or more types.

In the elastic wiring, a combination of a tube formed of silicone rubber and a conductor wire formed of SUS thread is particularly preferable.

The form of the conductor wire is not particularly limited, and for example may have the form of a single fiber or may have the form of a twisted thread in which a plurality of fibers are twisted together. In particular, the conductor wire 12 being in the form of interweaving strands is preferable from the standpoint of the conductor wire 12 having less of a tendency to spiral and become tangled in the tube 10 in an unextended state, and so can exist in a more stable state and allow smooth expansion and contraction of the elastic wiring 1.

The thickness of the conductor wire 12 can be set as appropriate, for example, 0.01 to 10 mm.

Note that when the conductor wire 12 is a twisted thread composed of a plurality of wires, the outer diameter thereof is defined as the thickness of the conductor wire 12.

An insulating coat may be applied to the surface of the conductor wire 12. Since the surface of the conductor wire 12 is coated with insulation, the impedance change accompanying expansion and contraction is reduced. As the insulating material used for the insulating coating, publicly known materials can be used. For example, polyurethane, polyesterimide, polyamideimide, poiimide, PVC (polyvinyl chloride mixture), PE (polyethylene) fluororesin, TUFRET (tufflet), and rubber can be used. As a method of insulating coating, a publicly known method can be adopted.

The conductor wire 12 may be coated with a lubricant such as silicone oil or a rust preventive material.

In the elastic wiring 1, the conductor wire 12 is arranged and fixed in the tube 10 so that the length L1 of the conductor wire 12 between the fixing portions when the tube 10 is not extended is longer than the length L2 of the tube 10 between the fixing portions. That is, the conductor wire 12 is arranged and fixed within the tube 10 so that, in the state of the tube 10 not being extended, the length L1 of the conductor wire 12 between the caulking members 14 is longer than the length L2 of the tube 10 between the caulking members 14, 14.

Figure 4:
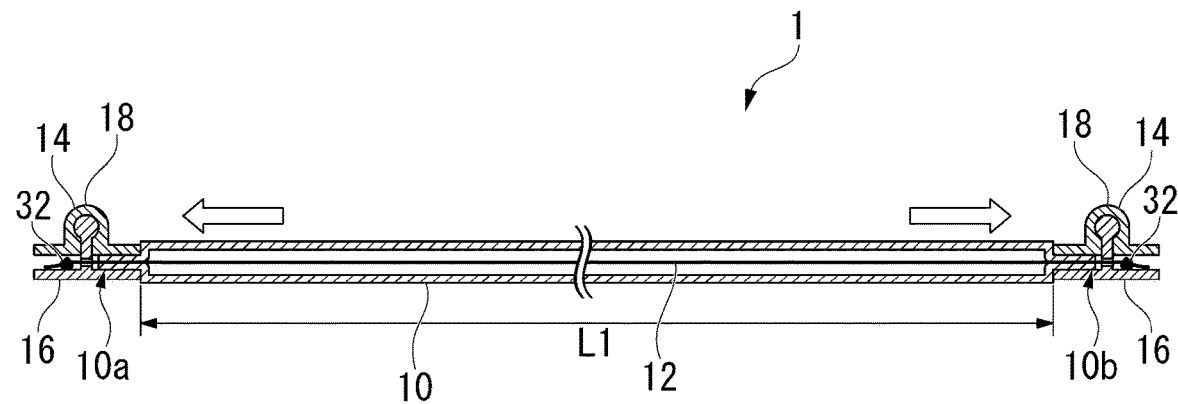
FIG. 4 is a cross-sectional view showing a state in which the elastic wiring of FIG. 2 is extended in the lengthwise direction.

Note that when the tube 10 is extended by pulling in the lengthwise direction thereof, putting the conductor wire 12 in a state of being linearly tensioned as shown in FIG. 4, the length L1 of the conductor wire 12 between the caulking members 14, 14 corresponds to the distance between the fixing portions by the caulking members 14 provided at both ends of the tube 10.

Because the length L1 of the conductor wire 12 between the fixing portions is longer than the length L2 of the tube 10 between the fixing portions, the conductor wire 12 takes on a shape having curves or bends so as to have a spiral shape or a zigzag shape in the tube 10 when the tube 10 is not extended. Thus, even if the conductor wire 12 itself is not substantially elastic, the conductor wire 12 is not strained by curving or bending within the tube 10 and has slack allowing extension in the lengthwise direction thereof. Therefore, the elastic wiring 1 can be extended by being pulled until the conductor wire 12 becomes linear as shown in FIG. 4, and when the tensile load is released, the conductor wire 12 contracts due to the elasticity of the tube 10 as shown in FIG. 2.

Further, in the expansion and contraction of the elastic wiring 1, since the conductor wire 12 either has a shape with curves or bends or is linear, there is little impedance fluctuation of the conductor wire 12 accompanying the stretching compared to a conductor wire including, for example, a conductive material mixed with an elastomer.

The ratio L1/L2 of the length L1 of the conductor wire 12 between the fixing portions to the length L2 of the tube 10 between the fixing portions in a state where the tube 10 is not extended is preferably 1.1 to 5, with 1.2 to 2 being more preferable. If the ratio L1/L2 is equal to or greater than the lower limit of the above range, excellent stretchability is easily obtained, and a sense of discomfort is further minimized. If the ratio L1/L2 is below the upper limit of the above range, manufacture of the elastic wiring 1 will be easy and productivity will become high.

The periphery of the conductor wire 12 in the tube 10 may be in a state in which air is present or in a state in which a liquid is filled therein. A state in which is air present is preferable from the standpoint of ease of manufacture of the elastic wiring 1.

The liquid to be filled around the conductor wire 12 in the tube 10 may be any liquid that does not inhibit movement of the conductor wire 12 within the tube 10 and that does not degrade the conductor wire 12, with examples including oil-based oil, silicone oil, glycerin, glycerol and the like.

Figure 3:
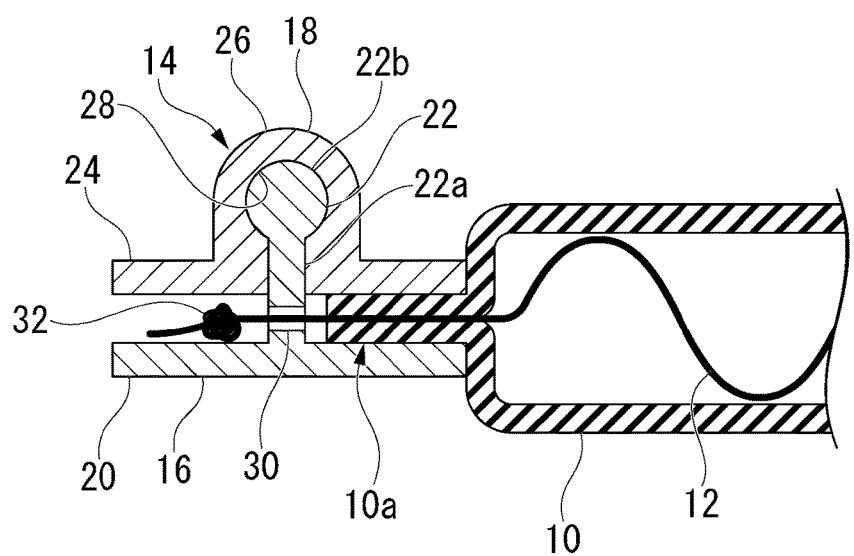
FIG. 3 is a cross-sectional view showing a caulking member provided at an end in the lengthwise direction of the elastic wiring of FIG. 2.

As shown in FIGS. 2 and 3, the caulking member 14 is provided with a male member 16 and a female member 18.

The male member 16 is provided with a disk-shaped first flat plate portion 20 and a fitting convex portion 22 provided so as to rise from the central portion of the first flat plate portion 20. The fitting convex portion 22 is provided with a trunk portion 22a that rises from the first flat plate portion 20, and a spherical head portion 22b that is provided at the tip of the trunk portion 22a.

The female member 18 is provided with a disk-shaped second flat plate portion 24 and a protrusion 26 provided on the center of the second flat plate portion 24, with a fitting concave portion 28 being formed in the protrusion 26. The fitting concave portion 28 opens at the lower surface of the second flat plate portion 24. The fitting concave portion 28 of the female member 18 is adapted to fit the head portion 22b of the fitting convex portion 22 of the male member 16.

In this way, the male member 16 and the female member 18 are configured such that the fitting convex portion 22 and the fitting concave portion 28 are detachably fitted.

At both end portions in the lengthwise direction of the tube 10, the tube 10 and the conductor wire 12 are caulked and fixed by the fitting convex portion 22 and the fitting concave portion 28 being fitted together so that the tube 10 and the conductor wire 12 are sandwiched by the first flat plate portion 20 of the male member 16 and the second flat plate portion 24 of the female member 18.

In the elastic wiring, it is preferable that the conductor wire and the tube be caulked and fixed by the caulking member as in this example, since the tube and the conductor wire can be easily and firmly fixed at the fixing portions at both ends of the tube. Moreover, it is more preferable that the conductor wire and the tube be caulked by the first flat plate portion of the male member and the second flat plate portion in a state where the male member and the female member of the caulking member are fitted together.

In this example, a through hole 30 is formed in the trunk portion 22a of the fitting convex portion 22 of the male member 16. At the first end portion 10a side of the tube 10, a portion of the conductor wire 12 exposed from the tube 10 is passed through the through hole 30, and a knot 32 larger than the through hole 30 is formed on the distal side of the conductor wire 12 that has passed through the through hole 30. In this state, the conductor wire 12 and the tube 10 are caulked by the male member 16 and the female member 18. Similarly, at the second end portion 10*b* side of the tube 10, a portion of the conductor wire 12 exposed from the tube 10 is passed through the through hole 30 and the knot 32 is formed. In this state, the conductor wire 12 and the tube 10 are caulked by the male member 16 and the female member 18.

In this way, in the elastic wiring, it is preferable to caulk the conductor wire and the tube in a state of the portion of the conductor wire exposed from the end of the tube being passed through the through hole of the caulking member, and a knot larger than the through hole being formed at the portion of the conductor wire that has passed through the through hole.

By passing the distal end side of the conductor wire 12 through the through hole 30 of the fitting convex portion 22 and forming the knot 32 thereon as in this embodiment, it is possible to prevent unexpected pullout of the conductor wire 12 when fixing the conductor wire 12 and the tube 10, and stably arrange the conductor wire 12 between the male member 16 and the female member 18. Therefore, the conductor wire 12 and the tube 10 can be more easily fixed by the caulking member 14, leading to an improved yield.

The material for forming the caulking member 14 is not particularly limited, and examples thereof include stainless steel (SUS), brass, copper, iron, silver, gold, platinum, aluminum, and tin. By forming the caulking member 14 with metal, it is possible to use the caulking member 14 as a termination that electrically connects to a terminal.

As the caulking member 14, for example, a snap button can be adopted.

A method for manufacturing the elastic wiring 1 includes the following method.

Figure 5A:
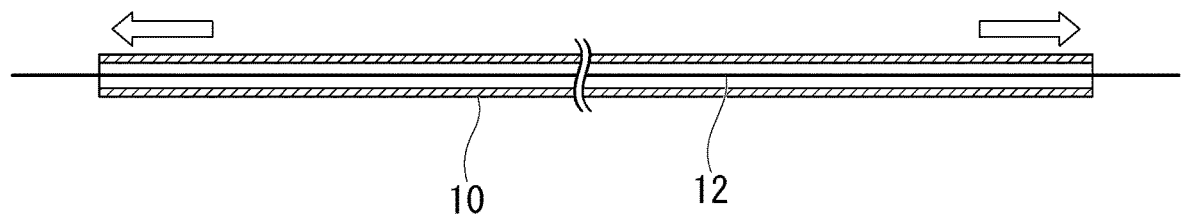
FIG. 5A is a sectional view showing a step of manufacturing the elastic wiring shown in FIG. 2.
Figure 5B:
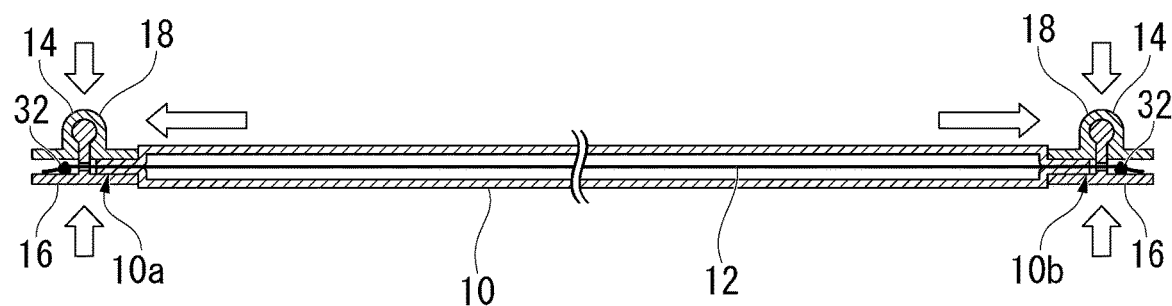
FIG. 5B is a cross-sectional view showing a step of manufacturing the elastic wiring shown in FIG. 2.
Figure 5C:
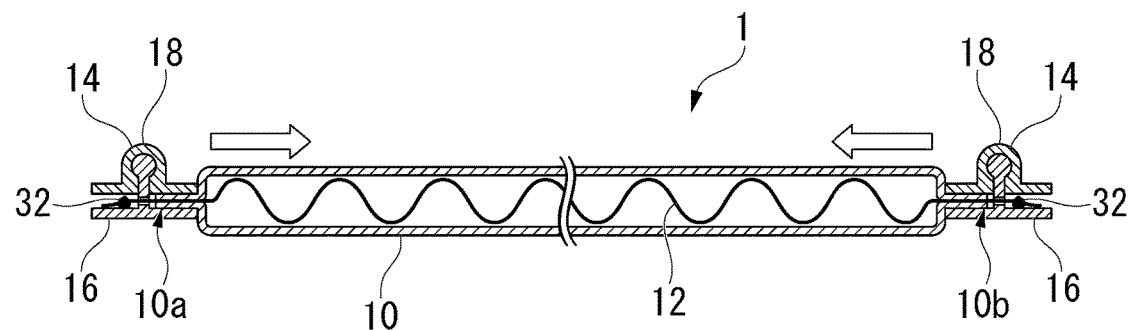
FIG. 5C is a sectional view showing a step of manufacturing the elastic wiring shown in FIG. 2.

As shown in FIG. 5A, the conductor wire 12 is passed through the tube 10 and loads pulling in the lengthwise direction are applied to the tube 10 so put the tube 10 in an extended state. In this state, as shown in FIG. 5B, the conductor wire 12 and the tube 10 are caulked and fixed by the caulking members 14 at both end portions in the lengthwise direction of the tube 10. Thereafter, as shown in FIG. 5C, by releasing the loads pulling the tube 10 and returning the tube 10 to the original unextended state, the elastic wiring 1 is obtained.

More specifically, an example will be described in which a silicon tube having an outer diameter of 2 mm and a wall thickness of about 0.2 mm is used as the tube 10 and a SUS (Steel Use Stainless) wire having a length of about 140 cm is used as the conductor wire 12. The thickness of the SUS wire (SUS304) is 12 μm and the mass is 0.22 g/m. The SUS wire is covered with the silicon tube, both ends of the silicon tube and the SUS wire are fixed, and the length of the tube and the SUS wire are contracted about 50%.

The elastic wiring 1 obtained in this way had a wire diameter of 2.5 mm and a length of 60 cm in a state of tension not being applied. When the elastic wiring 1 was tensioned in the lengthwise direction to be fully stretched, the length became 136 cm. The tension (initial motion sensitivity) when this elastic wiring 1 starts to be stretched was 0.03 Newton (N), and the tension required for complete stretching (maximum tension at the time of stretching) was 1.2 N. The DC resistance value of the SUS wire of the elastic wiring 1 was 30.5Ω, and no change in the resistance value due to the stretching was observed. When the elastic wiring 1 was completely extended and then the tension was released, the wire diameter was 2.5 mm and the length returned to 60 cm.

As described above, the elastic wiring 1 can be extended with a small tension. Accordingly, when worn by the subject together with clothes, the elastic wiring 1 extends without a sense of discomfort like a rubber string. Upon being extended with movement of the body when used as a wearable wiring, the elastic wiring 1 does not exert tension on a connected bioelectrode. Therefore, there is no shifting of the bioelectrode from the mounted position, and distortion of the signal obtained from the bioelectrode hardly occurs.

The wire diameter of this elastic wiring 1 is 2.5 mm, which is thinner than conventional cables. Moreover, by using the silicon tube as the tube, this elastic wiring 1 is flexible and soft to the touch. The elastic wiring 1 is attached to clothing and, even when in direct contact with skin, does not produce discomfort so is suitable for long-term biomedical measurement. The elastic wiring 1 using silicon and SUS wire is resistant to heat and chemicals, can be washed with a washing machine, and can be dried with a drying machine or a dryer.

When forming the knot 32 on the first end 10*a* side and the second end 10*b* side of the tube 10 by passing the portion exposed from the tube 10 of the conductor wire 12 through the through hole 30 in the manner of the elastic wiring 1 of the present embodiment, the operation may be performed with the tube 10 extended, or may be performed before the tube 10 is extended.

As methods for manufacturing the tube 10 and the conductor wire 12, publicly known methods can be used.

The sheath 110 is an elastic tube-shaped member. The same sheath 110 as the tube 10 of the elastic wiring 1 can be used except that the sheath 110 has a size capable of accommodating two pieces of the elastic wiring 1.

The inner and outer diameters of the sheath 110 are not particularly limited, and may be set as appropriate. What is necessary is just to set suitably according to the size and the number of pieces of wiring accommodated in the sheath 110.

The thickness of the sheath 110 is preferably from 0.1 to 3 mm, and more preferably from 0.2 to 1 mm. When the thickness of the sheath 110 is equal to or larger than the lower limit of the above range, sufficient strength is easily obtained. When the thickness of the sheath 110 is equal to or less than the upper limit of the above range, excellent elasticity is easily obtained.

Openings on a first end portion 110*a* side and a second end portion 110*b* side of the sheath 110 in the length direction thereof are sealed by sealing members 112A and 112B, respectively. Example materials for forming the sealing members 112A and 112B include insulating materials such as silicone, polyethylene, polyethylene terebutarate, rubber, fluorine resin, polyvinyl chloride mixture, polyimide, and epoxy resin.

In the composite wiring 100, on the first end portion 110*a* side in the length direction of the sheath 110, the two pieces of elastic wiring 1 are not connected to a terminal or the like. On the other hand, on the second end portion 110*b* side, the conductor wire 12 of each elastic wiring 1 can be connected to a terminal or the like.

The method of manufacturing the composite wiring 100 is not particularly limited. For example, the two pieces of elastic wiring 1 are bundled and inserted into the sheath 110, and the opening of the sheath 110 on the first end portion 110*a* side is sealed with the sealing member 112A. The opening on the second end portion 110*b* side of the sheath 110 is sealed with a sealing member 112B so that the pieces of elastic wiring 1 can be connected to a terminal or the like. Thereby, the composite wiring 100 is obtained.

Since each conductor wire can exist in a shape with slack having curves and bends within the tube of the respective elastic wiring in a non-extended state and the sheath has elasticity along with the tubes of the respective pieces of elastic wiring, the elasticity of the composite wiring described above is excellent. Further, the composite wiring of the present invention has excellent curl resistance. Therefore, even when applied to clothing, the elasticity of the fabric is hardly impaired, and discomfort when worn can be reduced. Further, since each conductor wire is respectively housed in the tubes of the elastic wiring, and the pieces of elastic wiring are housed in the sheath, the composite wiring of the present invention is also excellent in waterproofness.

The composite wiring of the present invention can handle various functions because a plurality of pieces of wiring are accommodated in the sheath. For example, in the composite wiring 100, the distance between the two pieces of elastic wiring 1 accommodated in the sheath 110 is maintained at substantially the same distance over the entire length in the lengthwise direction. Therefore, by connecting the composite wiring 100 to an IC circuit or the like that can detect a change in capacitance, the composite wiring 100 can be used as a capacitance sensor. The distance between the two pieces of elastic wiring 1 in the sheath 110 can be more stably maintained at the same distance by adjusting the size of the sheath 110 so that the gap between the peripheries of the two pieces of elastic wiring 1 in the sheath 110 is as small as possible.

As described above, the composite wiring of the present invention in which two pieces of elastic wiring are accommodated in the sheath as wiring can be used as a capacitance sensor. When the composite wiring of the present invention is used as a capacitance sensor, it is possible to detect, for example, wetness with water or a water level and the like by a change in capacitance. Specifically, by attaching the composite wiring of the present invention to a swimsuit as a capacitance sensor, it is possible to detect that the wearer has entered the water. Further, by attaching the composite wiring of the present invention to underwear as a capacitance sensor, it is possible to manage the amount of perspiration of the wearer.

The composite wiring of the present invention is not limited to the composite wiring 100 described above. For example, the number of pieces of wire accommodated in the sheath is not limited to two, and may be three or more. The number of pieces of wire housed in the sheath can be set appropriately according to the application.

In the composite wiring of the present invention, a non-elastic wiring other than the elastic wiring may be accommodated in the sheath in addition to the elastic wiring.

The composite wiring of the present invention is not limited to one in which a connection between the wiring and a terminal or the like can be made only at one end portion in the length direction as in the composite wiring 100. A connection between the wiring and a terminal or the like may be possible at both end portions.

Figure 6:
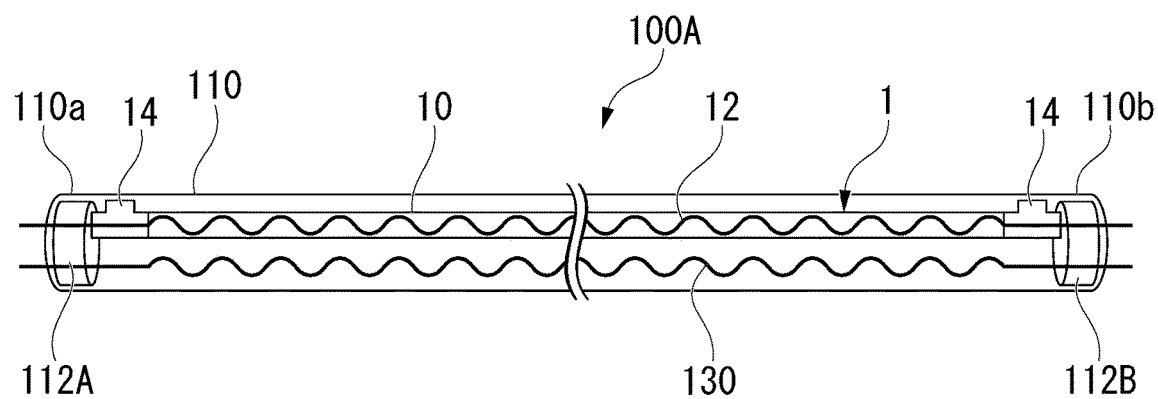
FIG. 6 is a side view showing the composite wiring according to another embodiment of the present invention.

For example, the composite wiring of the present invention may be the composite wiring 100A illustrated in FIG. 6. Portions in FIG. 6 that are the same as FIG. 1 are denoted by the same reference numerals, with descriptions thereof omitted. The composite wiring 100A is provided with a non-elastic wiring 130 in place of one of the two pieces of elastic wiring 1 in the composite wiring 100, and has the same mode as the composite wiring 100 except for connection with a terminal or the like being possible at both the first end portion 110a side and the second end portion 110b side of the sheath 110.

The non-elastic wiring 130 is not particularly limited, and a publicly known wire can be used. For example, a wiring formed from only the same conductor wire as the conductor wire 12 used in the elastic wiring 1 can be designated.

In this mode, it is preferable that the non-elastic wiring 130 exist in a shape having curves and bends within the sheath 110 in a non-extended state, in the same manner as the conductor wire 12 within the tube 10 in the elastic wiring 1, from the viewpoint of excellent elasticity being easily obtained.

Since the composite wiring 100A is provided with a plurality of pieces of wiring in the sheath 110, and connection with a terminal or the like is possible at both the first end portion 110a side and the second end portion 110b side of the sheath 110, use as a multiplexing cable is possible.

In this way, the composite wiring of the present invention can be used as a multiplexing cable because a plurality of pieces of wiring are accommodated and gathered together within the sheath. For example, the composite wiring of the present invention can be used as a multiplexing cable, with a plurality of electrodes for measuring biological signals such as electrocardiograms and electromyograms connected to one end portion, and a logger for writing data to an IC recorder or flash memory connected to the other end portion. When the composite wiring of the present invention is used as a multiplexing cable, the number of pieces of wiring accommodated in the sheath can be appropriately set according to the application, and can be, for example, 2 to 100.

In the composite wiring of the present invention, the pieces of wiring may be connected to each other via a notifying means or a measuring means in the sheath. Thereby, use is possible as wiring for incorporation into an element having a notifying function or measuring function of the notifying means or the measuring means.

The wiring for incorporation into an element may be provided with only one of the notifying means and the measuring means, or may be provided with both.

The notifying means may be any means capable of giving notification of desired information, with examples thereof including a light emitting element such as an LED, a vibrating element, and a sound generating element. As the notifying means, one type may be used alone, or two or more types may be used in combination.

The measuring means is not particularly limited provided accommodation in the sheath is possible, and examples thereof include a thermocouple and an acceleration sensor. As the measuring means, one type may be used alone, or two or more types may be used in combination.

Figure 7:
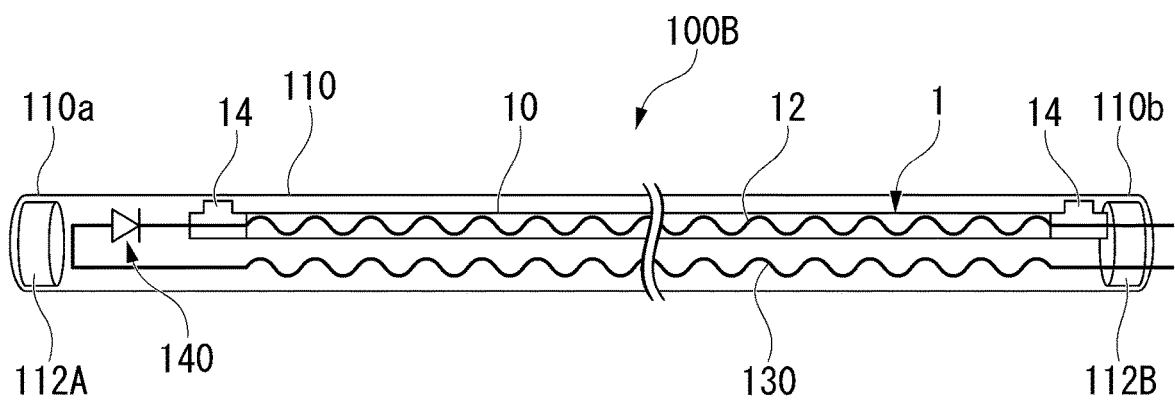
FIG. 7 is a side view showing the composite wiring according to still another embodiment of the present invention.

The composite wiring used as the wiring for incorporation into an element includes for example the composite wiring 100B illustrated in FIG. 7. The portions in FIG. 7 that are the same as those of FIG. 1 and FIG. 6 are denoted by the same reference numerals, and descriptions thereof will be omitted. The composite wiring 100B is the same mode as the composite wiring 100B except that the elastic wiring 1 and the non-elastic wiring 130 are connected via a light emitting element 140 on the first end portion 110a side in the sheath 110. The composite wiring 100B can be used as wiring for incorporation into an element having a notifying function provided by light emission of the light emitting element 140.

The composite wiring of the present invention may be wiring having two or three functions of any of a capacitance sensor, a multiplex cable, and a wiring for incorporation into an element.

The elastic wiring of the composite wiring of the present invention is not limited to the elastic wiring 1.

For example, the mode of fixing the tube and the conductor wire in the elastic wiring is not limited to a mode using the caulking member 14. The elastic wiring may be one in which the tube and the conductor wire are caulked and fixed by a caulking member in which the through hole 30 is not formed in the male member 16 of the caulking member 14.

Figure 8:
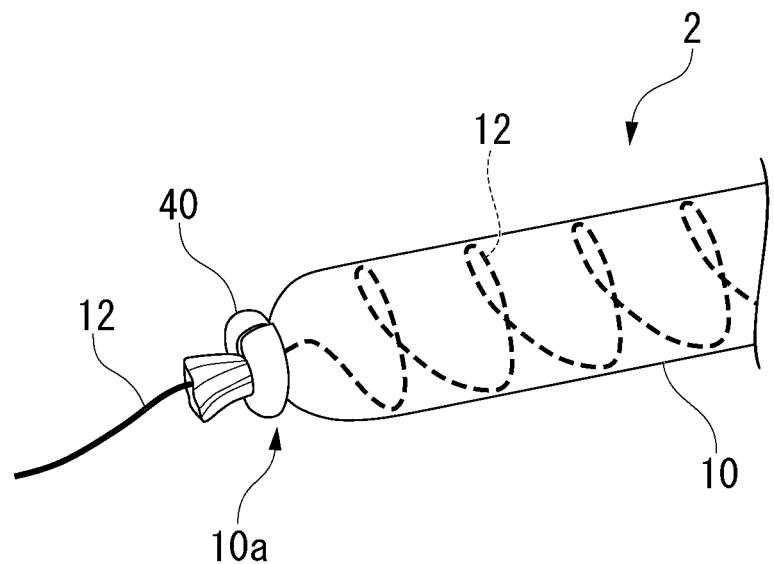
FIG. 8 is a perspective view showing the elastic wiring according to yet still another embodiment of the present invention.

The elastic wiring may be one in which the conductor wire and the tube are fixed by being stopped with a stopper. Specifically, for example, an elastic wiring 2 illustrated in FIG. 8 may be used.

The elastic wiring 2 has the same mode as the elastic wiring 1 except that the tube 10 and the conductor wire 12 are fixed by a stopper 40 instead of being fixed by the caulking member 14.

The stopper 40 is a rod-like fitting, being deformed into an annular shape so as to stop the conductor wire 12 and the tube 10 at a portion on the first end portion 10a side in the lengthwise direction of the tube 10. As described above, in the elastic wiring 2, the conductor wire 12 and the tube 10 are fixed by being stopped with the stopper 40 at the portion on the first end portion 10a side in the lengthwise direction of the tube 10. At the second end portion 10b side as well of the tube 10 in the lengthwise direction, the conductor wire 12 and the tube 10 are fixed by being stopped with the stopper 40.

Examples of the metal constituting the stopper 40 include SUS, brass, iron, and aluminum. The metal constituting the stopper 40 may be one type or two or more types.

The length and thickness of the stopper 40 may be set as appropriate as long as the conductor wire 12 and the tube 10 can be firmly fixed.

Figure 9:
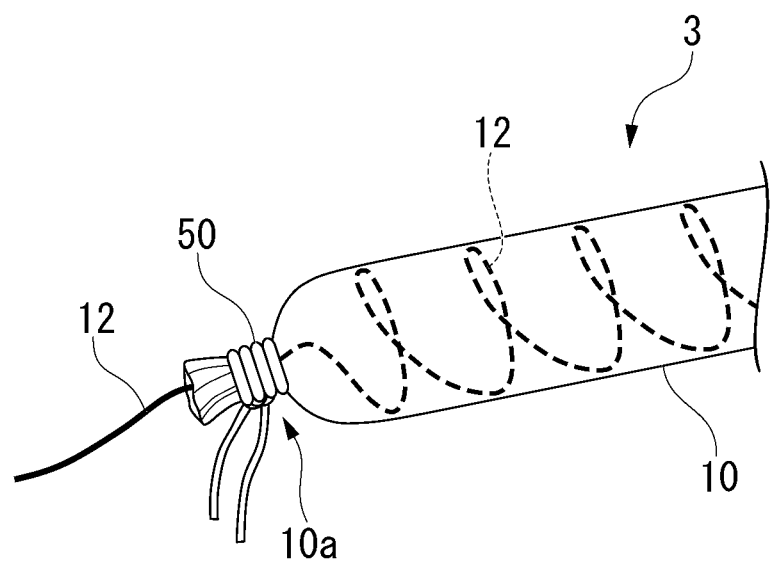
FIG. 9 is a perspective view showing an elastic wiring according to even yet still another embodiment of the present invention.

The elastic wiring may be one in which the conductor wire and the tube are fixed by being bound with a band material. Specifically, for example, an elastic wiring 3 illustrated in FIG. 9 may be used.

The elastic wiring 3 has the same mode as the elastic wiring 1 except that the tube 10 and the conductor wire 12 are fixed by a band material 50 instead of being fixed by the caulking member 14.

In the elastic wiring 3, the conductor wire 12 and the tube 10 are bound together and fixed by the band material 50 being wound and tied on a portion of the tube 10 on the first end portion 10a side thereof in the lengthwise direction. In addition, the conductor wire 12 and the tube 10 are bound together and fixed by the band material 50 being wound and tied on a portion of the tube 10 on the second end portion 10b side thereof in the lengthwise direction.

As the mode of the band material 50, any material can be used provided the band material 50 can bind and fix the conductor wire and the tube, and examples thereof include a binding band and a string. As the band material 50, one type may be used independently or two or more types may be used together.

The material for forming the band member 50 is not particularly limited, and examples thereof include polyethylene, polyethylene terephthalate, polyurethane, polystyrene, nylon, polycarbonate, fluorine resin, silicone rubber, and metals such as SUS, brass, iron, and aluminum.

The length and thickness of the band member 50 may be set as appropriate as long as the conductor wire 12 and the tube 10 can be firmly fixed.

The elastic wiring may be one in which a tube and a conductor wire are fixed by crimping using a crimping terminal. The crimping terminal may be any one capable of fixing the tube and the conductor wire by crimping, and a publicly known crimping terminal usually used for wiring can be employed.

Figure 10:
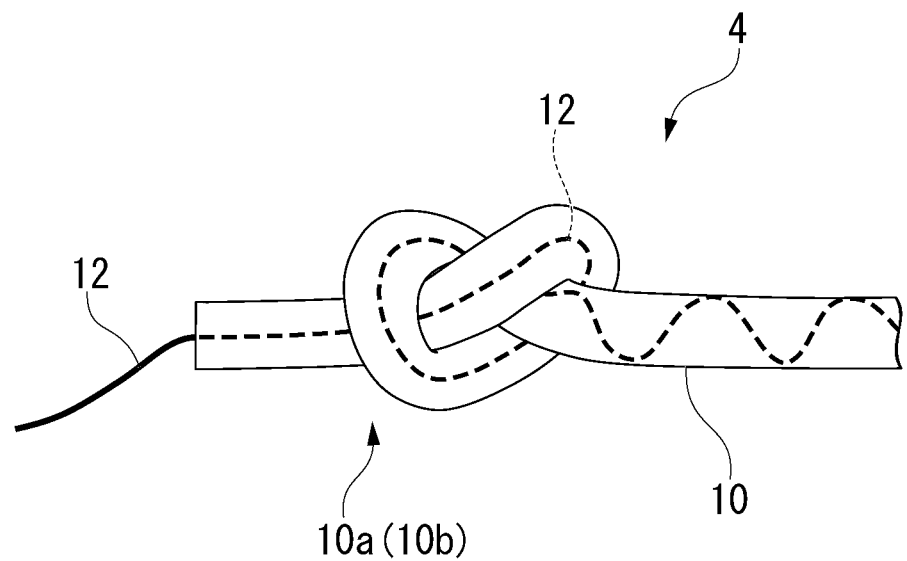
FIG. 10 is a side view showing the elastic wiring according to a yet still further embodiment of the present invention.

The elastic wiring may be an elastic wiring 4 in which, as shown in FIG. 10, the tube 10 and the conductor wire 12 are fixed by portions of the tube 10 on the first end portion 10a side and the second end portion 10b side in the lengthwise direction thereof being respectively knotted together with the conductor wire 12.

The elastic wiring may also be an elastic wiring in which the tube and the conductor wire are fixed by a pin terminal being inserted into both ends of the tube in the lengthwise direction thereof, with the portions of the tube in which the pin terminal has been inserted being bound with a string. The pin terminal is not particularly limited, and a publicly known crimping terminal normally used for wiring can be used.

As a mode of fixing the tube and the conductor wire in the elastic wiring, two or more of the above-described modes may be combined.

In the present invention, from the viewpoint of having excellent industrial productivity, a mode that caulks and fixes the tube and the conductor wire with the caulking member provided with the male member and female member such as the caulking member 14 is preferable among the above-described modes.

In the elastic wiring, the tube and the conductor wire may be fixed not only at both end portions of the tube but also at portions other than both end portions in the lengthwise direction of the tube. That is, the number of fixing portions at which the tube and the conductor wire in the elastic wiring are fixed is not limited to two, and may be three or more.

The composite wiring of the embodiment of the present invention including the above-described elastic wiring has excellent curl resistance and waterproofness as well as excellent elasticity. This composite wiring hardly impairs the elasticity of fabric even when applied to clothing, can reduce discomfort when worn, and is applicable to various functions.

Figure 11:
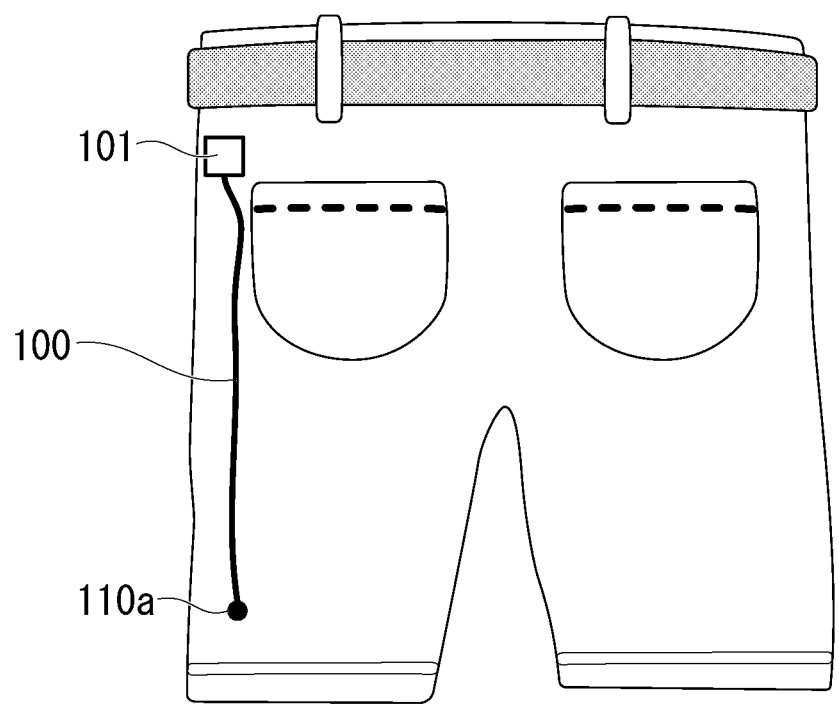
FIG. 11 is a front view showing a garment equipped with the composite wiring of one embodiment of the present invention.

FIG. 11 is a schematic view in which the composite wiring 100 of the embodiment is fixed to a garment. A transmitter 101 is connected to the second end portion 110b of the composite wiring 100 shown in FIG. 1, while the first end portion 110a is fixed to a garment. In this case, the composite wiring 100 forms a kind of capacitance sensor. As a result, the composite wiring 100 can monitor biological components such as the degree of wetness of the clothing and sweat of the wearer as a change in capacitance, and can transmit data to the outside by the transmitter 101.

The composite wiring 100 may be arranged inside or outside of the garment depending on the purpose. In addition to the trousers shown in FIG. 11, the garment may be of any type, such as a muffler, a bandage, or a sock, as long as the composite wiring 100 of the present embodiment can be fixed thereto, and any method of fixing the wiring may be used.

The method of fixing the transmitter 101 and the first end portion 110a, as well as the fixing position may be arbitrarily determined. For example, different clothes may be straddled, such as fixing the transmitter 101 to trousers and fixing the first end portion 110a to a sock.

DESCRIPTION OF THE REFERENCE SYMBOLS

1-4: Elastic wiring
10: Tube
10a: First end portion

10b: Second end portion
12: Conductor wire
14: Caulking member
16: Male member
18: Female member
20: First flat plate portion
22: Fitting convex portion
22a: Trunk portion
22b: Head portion
24: Second flat plate portion
26: Protrusion
28: Fitting convex portion
30: Through hole
32: Knot
40: Stopper
50: Band material
100, 100A, 100B: Composite wiring
110: Sheath
110a: First end portion
110b: Second end portion
130: Non-elastic wiring
140: Light emitting element

The invention claimed is:

1. A composite wiring comprising a plurality of pieces of wiring accommodated and gathered together within an elastic sheath, wherein at least one of the pieces of wiring is elastic wiring comprising an elastic tube, a conductor wire arranged within the tube and having slack in the tube, thereby allowing extension of the conductor wire in a lengthwise direction of the conductor wire, and fixing portions for fixing the conductor wire and the tube at both ends of the tube in the lengthwise direction thereof, wherein
the length of the conductor wire between the fixing portions when the tube is in an unextended state being longer than the length of the tube between the fixing portions, and
the fixing portion includes a male member having a first flat plate portion and a fitting convex portion provided with a through hole, and a female member having a second flat plate portion facing the first flat plate portion and a fitting concave portion to be fitted to the fitting convex portion, the both ends of the conductor wire and the tube are caulked by the first flat plate portion and the second flat plate portion by forming a knot larger than the through hole on a distal side of the conductor wire that has passed through the through hole and fitting the fitting convex portion of the male member and the fitting concave portion of the female member.

2. A capacitance sensor formed from a composite wiring comprising a plurality of pieces of wiring accommodated and gathered together within an elastic sheath, wherein at least one of the pieces of wiring is elastic wiring comprising an elastic tube, a conductor wire arranged within the tube and having slack in the tube, thereby allowing extension of the conductor wire in a lengthwise direction of the conductor wire, and fixing portions for fixing the conductor wire and the tube at both ends of the tube in the lengthwise direction thereof, wherein
the length of the conductor wire between the fixing portions when the tube is in an unextended state being longer than the length of the tube between the fixing portions, and
the fixing portion includes a male member having a first flat plate portion and a fitting convex portion provided with a through hole, and a female member having a second flat plate portion facing the first flat plate portion and a fitting concave portion to be fitted to the fitting convex portion, the both ends of the conductor wire and the tube are caulked by the first flat plate portion and the second flat plate portion by forming a knot larger than the through hole on a distal side of the conductor wire that has passed through the through hole and fitting the fitting convex portion of the male member and the fitting concave portion of the female member, and
two pieces of elastic wiring are accommodated in the sheath as the wiring.

3. A multiplexing cable formed from a composite wiring comprising a plurality of pieces of wiring accommodated and gathered together within an elastic sheath, wherein at least one of the pieces of wiring is elastic wiring comprising an elastic tube, a conductor wire arranged within the tube and having slack in the tube, thereby allowing extension of the conductor wire in a lengthwise direction of the conductor wire, and fixing portions for fixing the conductor wire and the tube at both ends of the tube in the lengthwise direction thereof, wherein,
the length of the conductor wire between the fixing portions when the tube is in an unextended state being longer than the length of the tube between the fixing portions, and
the fixing portion includes a male member having a first flat plate portion and a fitting convex portion provided with a through hole, and a female member having a second flat plate portion facing the first flat plate portion and a fitting concave portion to be fitted to the fitting convex portion, the both ends of the conductor wire and the tube are caulked by the first flat plate portion and the second flat plate portion by forming a knot larger than the through hole on a distal side of the conductor wire that has passed through the through hole and fitting the fitting convex portion of the male member and the fitting concave portion of the female member.

4. A wiring for incorporation into an element formed from a composite wiring comprising a plurality of pieces of wiring accommodated and gathered together within an elastic sheath, wherein at least one of the pieces of wiring is elastic wiring comprising an elastic tube, a conductor wire arranged within the tube and having slack in the tube, thereby allowing extension of the conductor wire in a lengthwise direction of the conductor wire, and fixing portions for fixing the conductor wire and the tube at both ends of the tube in the lengthwise direction thereof, wherein
the length of the conductor wire between the fixing portions when the tube is in an unextended state being longer than the length of the tube between the fixing portions,
the fixing portion includes a male member having a first flat plate portion and a fitting convex portion provided with a through hole, and a female member having a second flat plate portion facing the first flat plate portion and a fitting concave portion to be fitted to the fitting convex portion, the both ends of the conductor wire and the tube are caulked by the first flat plate portion and the second flat plate portion by forming a knot larger than the through hole on a distal side of the conductor wire that has passed through the through hole and fitting the fitting convex portion of the male member and the fitting concave portion of the female member, and
pieces of wiring are connected to each other via a notifying means or a measuring means in the sheath.

5. A garment to which a composite wiring is fixed, the composite wiring comprising a plurality of pieces of wiring accommodated and gathered together within an elastic sheath, wherein at least one of the pieces of wiring is elastic wiring comprising an elastic tube, a conductor wire arranged within the tube and having slack in the tube, thereby allowing extension of the conductor wire in a lengthwise direction of the conductor wire, and fixing portions for fixing the conductor wire and the tube at both ends of the tube in the lengthwise direction thereof, wherein the length of the conductor wire between the fixing portions when the tube is in an unextended state being longer than the length of the tube between the fixing portions, and the fixing portion includes a male member having a first flat plate portion and a fitting convex portion provided with a through hole, and a female member having a second flat plate portion facing the first flat plate portion and a fitting concave portion to be fitted to the fitting convex portion, the both ends of the conductor wire and the tube are caulked by the first flat plate portion and the second flat plate portion by forming a knot larger than the through hole on a distal side of the conductor wire that has passed through the through hole and fitting the fitting convex portion of the male member and the fitting concave portion of the female member.

6. The garment according to claim 5, further comprising a transmitter connected to one end of the composite wiring.

\* \* \* \* \*